United States Patent
Feiweier et al.

(10) Patent No.: US 8,195,417 B2
(45) Date of Patent: Jun. 5, 2012

(54) METHOD FOR RECORDING MEASURED DATA FROM A PATIENT BY TAKING MOVEMENTS INTO ACCOUNT, AND ASSOCIATED MEDICAL DEVICE

(75) Inventors: Thorsten Feiweier, Poxdorf (DE); Ralf Ladebeck, Erlangen (DE); Diana Martin, Herzogenaurach (DE); Hartwig Newiger, Nürnberg (DE); Josef Pfeuffer, Newton, MA (US); Michael Szimtenings, Bonn (DE); Harald Werthner, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 426 days.

(21) Appl. No.: 12/219,610

(22) Filed: Jul. 24, 2008

(65) Prior Publication Data
US 2009/0037130 A1 Feb. 5, 2009

(30) Foreign Application Priority Data
Jul. 26, 2007 (DE) .......................... 10 2007 034 955

(51) Int. Cl.
*G01R 35/00* (2006.01)
(52) U.S. Cl. ........................................................ 702/95
(58) Field of Classification Search ...................... 702/95
See application file for complete search history.

(56) References Cited

U.S. PATENT DOCUMENTS
2006/0266947 A1 11/2006 Krieg et al.

FOREIGN PATENT DOCUMENTS
DE 10 2005 023 907 12/2006

OTHER PUBLICATIONS

Richard D. Beach, Feasibility of Stereo-Infrared Tracking to Monitor Patient Motion During Cardiac SPECT Imaging, 2004 IEEE, pp. 2144-2148.*
http://en.wikipedia.org/wiki/K-space_(topology), p. 1, Aug. 6, 2010.*
Timo Mäkelä, A Review of Cardiac Image Registration Methods, IEEE Transactions on Medical Imaging, vol. 21, No. 9, Sep. 2002, pp. 1011-1021.*
H. A. Ward et al.: Prospective Multiaxial Motion Correction for MRI, Magnetic Resonance in Medicine 43 (2000), Seiten 459-469: Book.

* cited by examiner

*Primary Examiner* — Tung S Lau
(74) *Attorney, Agent, or Firm* — Harness, Dickey & Pierce, P.L.C.

(57) ABSTRACT

Disclosed is a method and apparatus for recording measured data from a patient by taking movements into account by use of a medical device designed both for recording motion-related measured data and for recording nuclear medicine measured data. The method may include recording nuclear medicine measured data by use of the medical device, simultaneously recording motion-related measured data by use of the medical device, determining at least one motion information item relating to at least one movement of the patient and/or at least one movement inside the body of the patient during the ongoing measured data recording by evaluating at least a portion of the previously recorded motion-related measured data, and carrying out motion correction for at least a portion of the nuclear medicine measured data by use of the computational device in parallel with recording the measured data.

20 Claims, 3 Drawing Sheets

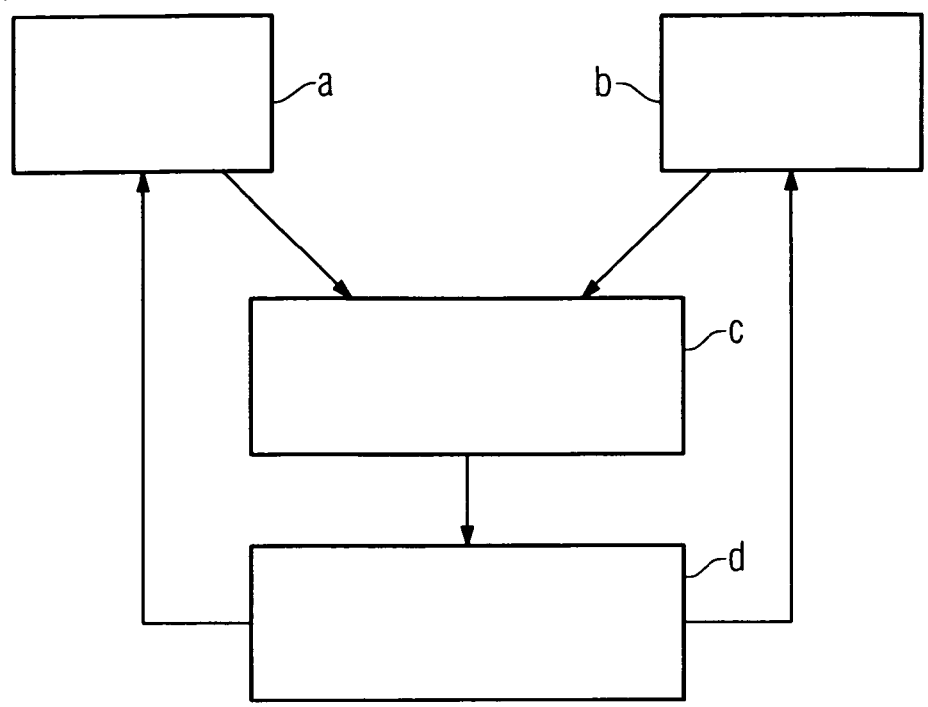
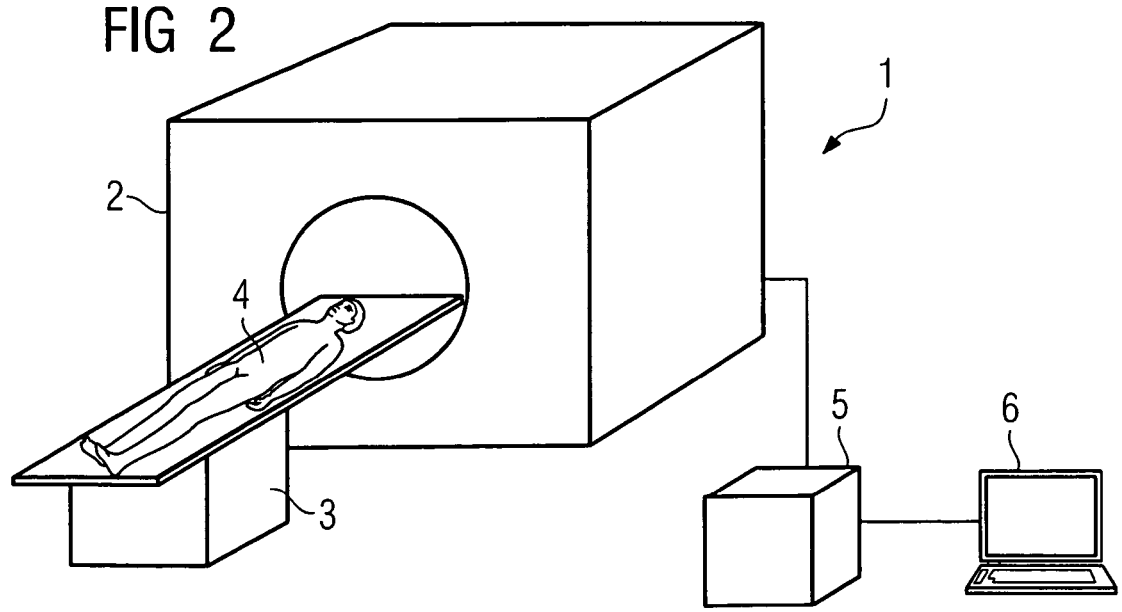

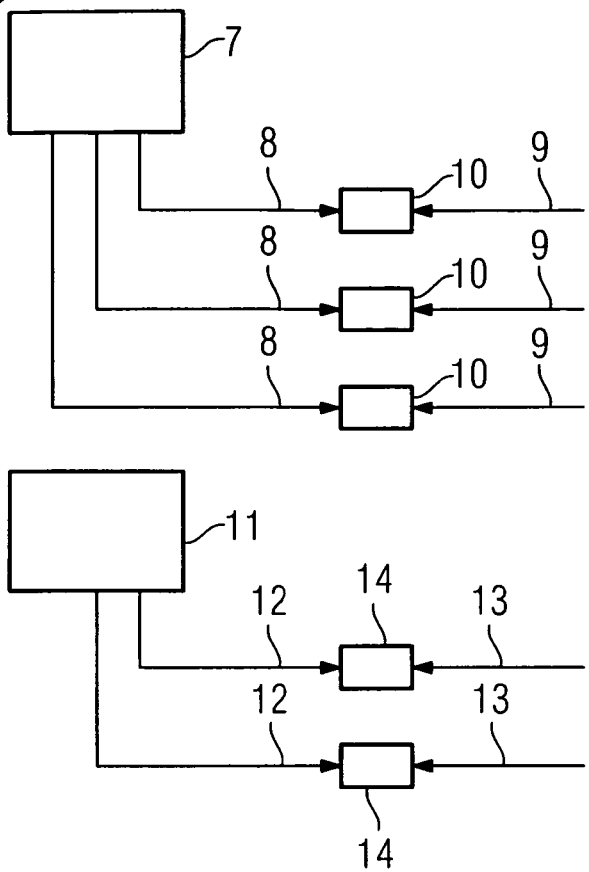
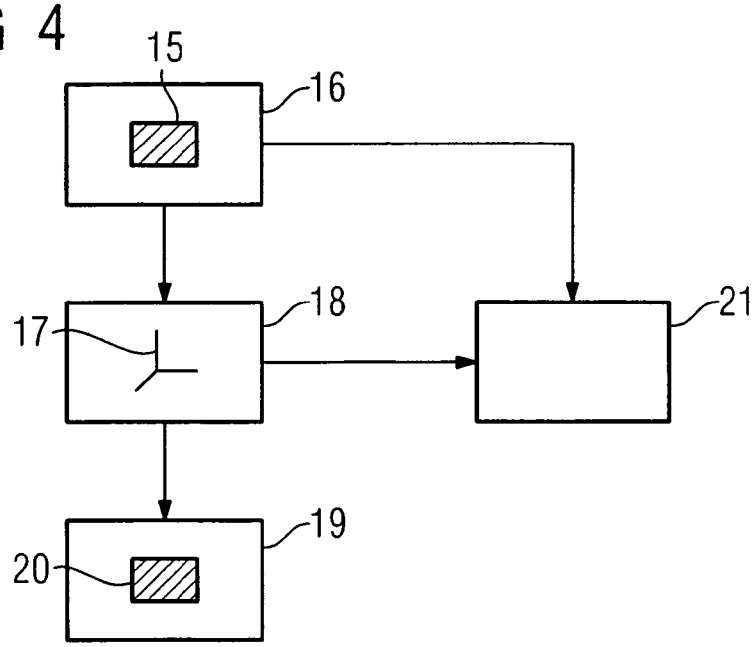

METHOD FOR RECORDING MEASURED DATA FROM A PATIENT BY TAKING MOVEMENTS INTO ACCOUNT, AND ASSOCIATED MEDICAL DEVICE

PRIORITY STATEMENT

The present application hereby claims priority under 35 U.S.C. §119 on German patent application number DE 10 2007 034 955.8 filed Jul. 26, 2007, the entire contents of which is hereby incorporated herein by reference.

FIELD

Embodiments of the invention generally relate to a method for recording measured data from a patient. For example, an embodiment relates to a method for recording measured data from a patient by taking movements into account by way of a medical device designed both for recording motion-related measured data, in particular measured data with a high temporal resolution and/or measured data which can be interpolated with regard to movements, using an imaging method and/or by way of at least one sensor element and for recording nuclear medicine measured data, in particular with a relatively low temporal resolution, and also to an associated medical device.

BACKGROUND

In recent times, so-called hybrid modalities are increasingly being used in medical imaging; for example, modalities designed for the simultaneous recording of computed tomography and positron emission tomography data (PET data), or modalities by which it is possible to create both magnetic resonance records and also positron emission tomography records, or magnetic resonance records and single photon emission computed tomography records (SPECT records). Other hybrid modalities are also feasible, for example a modality which is able to create both computed tomography records (CT records) and also SPECT records.

These hybrid modalities advantageously respectively provide a combination of at least one modality with a high temporal or spatial resolution (for example, magnetic resonance imaging (MRI) or CT) and at least one modality with a high sensitivity (for example, SPECT or positron emission tomography (PET) or another nuclear medicine method).

In the case of nuclear medicine images, the problem namely exists that the resolution is limited by different factors, for example by the motion of the patient during the data acquisition. On the other hand, methods such as magnetic resonance imaging have high anatomical accuracy and/or a high temporal resolution. For this reason, additional magnetic resonance imaging recording or computed tomography recording or the like is carried out in addition to the nuclear medicine recording of data in the case of hybrid modalities.

Until now it was the case that a sensible compromise was sought for the duration of the data acquisition when recording nuclear medicine data. The acquisition time should be long enough to detect a sufficient number of events, but, on the other hand, it should be short enough for the patient to be able to lie still during it. The influences of the respiratory or cardiac motions have been limited by different methods, for example by gating methods in which measured data are recorded, by way of example, only during the exhalation phase. Furthermore, there are different approaches to following the motion of the patient using optical systems so that they can subsequently be incorporated into the reconstruction of the nuclear medicine data.

However, the ability of such methods to achieve improvements in the image record is limited, or they require considerable technical complexity.

SUMMARY

In at least one embodiment of the invention, a method is disclosed for motion correction which is improved in this respect, in particular being more exact and clinically more useful.

In at least one embodiment, a method is provided, with comprising:
  recording nuclear medicine measured data by means of the medical device,
  simultaneously recording motion-related measured data by means of the medical device,
  determining at least one motion information item relating to at least one movement of the patient and/or at least one movement inside the body of the patient during the ongoing measured data recording by evaluating at least a portion of the previously recorded motion-related measured data by means of a computational device of the medical device, and
  carrying out motion correction for at least a portion of the nuclear medicine measured data in real-time by means of the computational device in parallel with recording the measured data depending on the at least one determined motion information item.

The existing possibility of being able to simultaneously (at the same time or in parallel) record both nuclear medicine data and also, if appropriate, high-resolution temporal and spatial data, for example by way of a magnetic resonance imaging scanner or a computed tomography scanner, is used in a targeted manner, in particular when using hybrid modalities as medical imaging devices. This allows an examination volume to be imaged simultaneously and, if appropriate, even isocentrically, for example by using an MRI/PET modality or an MRI/SPECT modality. If appropriate, the motion-related measured data is not image data, but rather it is sensor data, for example, by which motion information can also be derived by a medical device with corresponding sensors. If the temporal resolution of the motion detection is not high enough, it is possible to interpolate between two instances of motion detection.

By way of the high-resolution data, for example with regard to time and anatomy, of an imaging method with a high temporal resolution it is possible to log the patient motion during the examination and to correct the nuclear medicine data accordingly. As a result of this, the image quality of the nuclear medicine images can be significantly improved. By way of example, this is advantageous in the case of unavoidable motion, such as cardiac motion, respiration, or a bowel motion. Likewise, this is advantageous in the case of patients who are particularly agitated or uncooperative or who are unable to lie still for a certain amount of time due to their illness.

Thus, at least one motion information item is determined or extracted from the motion-related measured data, which preferably has a high temporal resolution and which is already available at that moment in time, that is to say from magnetic resonance imaging data, for example, during the recording of the measured data by way of a computational device of the hybrid modality. By way of example, this information can relate to the respiratory motion of the patient.

At least one motion correction information item is derived from this information in parallel with the ongoing recording of the measured data. Hence, an entrained motion correction is carried out in real-time. Evaluation of the already present temporally high-resolution data, or at least of a portion of the data, is carried out entrained to the data acquisition to obtain correction information with respect to movements that may have occurred, the evaluation being carried out in step with the acquisition.

The determined motion correction is thus carried out directly during the measurement, which is to say in real-time.

Of course, correction is required only in the case of motion actually having taken place. If an evaluation is carried out or motion information is determined in such a manner that the body region of the patient relevant to the record has not moved, then the motion correction is accordingly carried out such that no change is effected with regard to possibly previously determined motion information and continues to be the basis for motion correction, or, in the case of initially determined motion information, no continued correction of the data is carried out.

Within the scope of the method according to at least one embodiment of the invention, it is thus possible to correct the nuclear medicine images, which could be PET images with a resolution in the region of three millimeters, for example, in an effective manner with regard to movements of the patient, or within the body of the patient. The precision of the detection is required to be in the region of approximately one millimeter for this purpose. This corresponds to an angular resolution of rotational motions in the region of 0.3 degrees for a field of view of five hundred millimeters.

It is in any case fundamental to at least one embodiment of the invention that the motion correction is in principle carried out in an entrained manner in real-time.

According to at least one embodiment of the invention, it is possible for the motion correction to be carried out prospectively, in particular such that motion correction for newly recorded measured data is carried out depending on a determined motion information item until a corresponding new motion information item is present, and/or for a determined motion information item for carrying out motion correction for newly recorded measured data to be adapted.

The motion correction is thus carried out in an anticipatory manner. As soon as the current motion state is known, it is applied in real-time to the subsequently incoming nuclear medicine data until, for example, new motion information is present. This affords the advantage that incoming data can be processed directly without a waiting time. Even in the case of possible cancelation of a data recording, all recorded and saved nuclear medicine data, all the PET measured data, for example, is already motion-corrected. This prospective motion correction is thus carried out in real-time during the ongoing measurement. Correspondingly, motion information already being used to carry out motion correction can be changed or adapted prospectively. The newly recorded measured data is then corrected by the correspondingly changed motion information, or on the basis of this changed motion information.

Moreover, motion correction can additionally be carried out for at least a portion of the motion-related measured data, for example for such measured data having a high temporal resolution. Hence, it is possible not only to correct the nuclear medicine data with regard to the motion of the patient or a body part of the patient, but also to use the motion information or the one motion information item to likewise undertake motion correction for the motion-related measured data, for example the magnetic resonance data.

By way of example, such motion correction can mean entraining a standardized image of a method with a high temporal resolution. If the motion information is always recorded with respect to a fixed standardized image, then under certain circumstances it is possible that the problem of it becoming more and more difficult to determine the information precisely and reliably appears in the case of larger motion amplitudes. It is thus advantageous to also prospectively correct the records which serve for detecting motion.

By way of example, such motion correction can be carried out such that a reference coordinate system for recording the motion-related measured data with a high temporal resolution, or for interpolation, is entrained to the record of the motion-related measured data. By way of example, a reference coordinate system in which the magnetic resonance images are recorded can be entrained to each detected motion.

According to at least one embodiment of the invention, the motion correction for at least a portion of the nuclear medicine measured data in this case is carried out taking into account the translation and/or rotation of the reference coordinate system, and the translation and/or rotation of at least one recording object in the reference coordinate system. As long as they are nuclear medicine data, the records which relate to a particular examination region of the patient or an object to be recorded, such as the heart, or a particular body region or the patient overall are thus motion corrected in such a fashion that, on the one hand, the change of the reference coordinate system, and, on the other hand, the motion of the object with regard to this coordinate system are taken into account.

For the images of the method having a high temporal resolution or for the recording of the motion-related measured data overall, the entrainment of the reference coordinate system provides the advantage that the images always look very similar, independently of the respective motion amplitude, so that reliably registering a current motion state is simplified.

According to at least one embodiment of the invention, magnetic resonance imaging data and/or computed tomography data and/or ultrasound data and/or sensor data from at least one optical and/or electrical sensor element in particular, can be recorded as motion-related measured data; and/or positron emission tomography data and/or single photon emission computed tomography data can be recorded as nuclear medicine measured data. It is of course likewise possible to use recording methods not mentioned here. Care has to be taken in the process to ensure that the resolution is high enough in the temporally high-resolution methods in order to permit motion correction of the nuclear medicine data, or that the motion-related measured data permits interpolation if the temporal resolution is lower. It is thus possible, if appropriate, to (at least additionally) also use ultrasound methods or optical and/or electrical and also other motion detectors, for example. Of course, hybrid modalities which allow recording of data by more than two methods can be used. By way of example, a hybrid modality can permit magnetic resonance imaging recording and also additionally permit the recording of PET and SPECT data.

It is particularly advantageous that when recording magnetic resonance data as temporally high-resolution motion-related measured data, for example, at least one motion information item can be determined in reciprocal k-space. Accordingly, motion information (in the case of magnetic resonance imaging, but in principle also in the case of other imaging methods which permit this) is determined in Fourier space rather than in the image space. This permits particularly fast data recording or evaluation. In this case it suffices to record data in a small portion of Fourier space in order to determine the motion information. No image can be generated from this data, but reliable motion information can be extracted.

In particular, the motion information items or the plurality of motion information items can be determined in k-space on the basis of at least one recorded navigation scan. It is possible to obtain information about the rigid body motion in k-space by way of very fast navigation scans or orientation scans. A few milliseconds suffice for the navigation scans. Accordingly, temporally very high-resolution motion corrections are correspondingly possible. The navigator recordings can serve solely for determining motion data. A rigid body motion can be measured and determined quickly using orbital, spherical or cloverleaf navigators. The recording duration of a single navigator lies in the order of milliseconds, with it being possible to incorporate the navigator recording into a standard magnetic resonance imaging procedure without too many problems. The navigators are thus recorded within a clinical imaging sequence (for obtaining anatomical data, for example), or before or after clinical recordings.

It is particularly advantageous for the motion-related measured data and the nuclear medicine measured data to be recorded isocentrically and/or with synchronized timestamps. The simultaneous and isocentric recording permits particularly exact motion correction. Errors are avoided by means of synchronized timestamps. If the data recording is isocentric and effected with synchronized timestamps, the accuracy of the motion correction and the motion detection can be controlled in a targeted manner by the temporal resolution of image records from a method with a high temporal resolution.

At least one imaging specification for the motion correction can be determined from the at least one motion information item or a multiplicity of determined motion information items, in particular within the scope of automatic motion detection for the measured data recording with a high temporal resolution. The movements of the patient, or within the body of the patient, can thus be converted into imaging specifications, taking timestamps into account, which are then used for nuclear medicine image reconstruction. By way of example, conventional clinical magnetic resonance measurements can be carried out during the nuclear medicine data acquisition, with the translation and rotation parameters, for example in the case of rigid motion correction, being determined by means of a suitable coregistration function (for example, in fusion-software). The measurement time of the respective magnetic resonance sequence serves as a timestamp. This information is then transferred to the nuclear medicine reconstruction as an imaging specification. The data from a magnetic resonance attenuation correction measurement can likewise be used for motion detection, just like the clinical magnetic resonance measurements.

The motion information thus serves to define an image which is subsequently used for data correction entrained to the data acquisition.

Furthermore, at least one motion information item can be determined by using at least one motion detection module provided for recording the motion-related measured data and/or by using at least one measured data record carried out using a reduced spatial resolution, and/or can be determined within the scope of a keyhole measured data record. Hence, the most varied motion detection methods can be used on their own or in combination, in particular the most varied motion detection methods originating from magnetic resonance imaging.

By way of example, so-called "motion navigators" should be mentioned as motion detection modules, which serve for automatic detection of patient motion during the magnetic resonance imaging sequences. In this case, the patient motion is immediately taken into account in the magnetic resonance data acquisition by means of an additional motion navigator signal. An example is the 3D-motion correction in the case of sequences in the field of echo planar imaging (EPI). The 3D-motion correction in EPI can be carried out using navigators using orbital, spherical or cloverleaf navigators, for example. In addition, the recorded image data itself can be used for the motion detection. Here, the fact that a complete volume record is acquired within a couple of seconds in the case of EPI is utilized and motion can thus be detected with a high temporal and sufficient spatial resolution. The EPI images are used additionally or mainly for diagnostic purposes. The motion-related specifications, which are determined and used during magnetic resonance data acquisition, are used as imaging specifications for the nuclear medicine motion correction. Motion correction with a high temporal resolution can thus be carried out.

Moreover, it is possible to repeatedly generate images with a reduced resolution during acquisition, for example by means of a method having a high temporal (spatial) resolution, for example a magnetic resonance method. By way of example, using certain methods, a low resolution image can be extracted from each readout and its data can be used for motion correction. This still affords higher temporal resolution than in the case of only coregistering between clinical images. Accordingly, keyhole imaging methods can be used in which only the central k-space region is recorded anew for each image.

According to at least one embodiment of the invention, rigid and/or elastic motion correction can be carried out. In this case, the rigid motion correction relates to rigid body motion, which is prescribed by the three translational and three rotational degrees of freedom of the rigid body. By way of example, elastic motion correction is required in the case of respiration or cardiac motion. In this case an image specification for the motion correction is correspondingly more complex. In the case of periodic motions, such as respiration, a motion cycle can be recorded in advance with a high temporal resolution, for example by means of magnetic resonance imaging. A cyclical imaging scheme can be developed from this. During the ongoing nuclear medicine examination, only the phase then needs to be determined and the imaging specification needs to be assigned. Using this, time consuming and complex algorithms can be dispensed with during the actual measured data recording. The cyclical motion correction can additionally be combined with rigid motion correction so as thus to acquire all relevant motions.

Within the scope of the simultaneous recording of the motion-related measured data, at least one standard measurement protocol and/or at least one attenuation correction measurement and/or at least one navigation scan, in a particular a three-dimensional measurement and/or a two-dimensional multi-layer measurement and/or a measurement of three orthogonal layers and projections, can be recorded, in particular at predetermined points in time and/or at fixed time intervals.

By way of example, it is thus possible to record a magnetic resonance orientation scan at particular points in time. By way of example, it is possible to carry out a fast three-dimensional measurement, or a comparable measurement with a recording time of a few seconds, prior to each clinical magnetic resonance measurement. This measurement can supply motion information in addition to diagnostic information, if appropriate. This makes more exact co-registration possible, since the same volumes are always recorded with the same magnetic resonance imaging contrast. The imaging specification results from the coregistration data and the timestamps of the orientation measurements.

Moreover, a navigation or orientation scan can always be carried out at determined constant times, even during a presently ongoing clinical computed tomography or magnetic resonance measurement, for example. The ongoing sequence is briefly interrupted at a location that is not important to the image quality, or independent thereof, and is continued after the orientation scan has been recorded.

Moreover, data from the attenuation correction measurements present can be used for motion detection. It is also possible to use the recording sequences, from a plurality of repetitions, for example, by means of which a patient motion is detected automatically. This can then be taken into account immediately during the further acquisition of data, which is to say in the following repetitions, using a method with a high temporal resolution, for example. By way of example, three-dimensional motion correction can be used as in the case of echo planar imaging sequences.

These different methods of recording measured data can be used on their own or in combination with one another. In the case of the orientation or navigation scans, it is possible for the coregistration to be optimized by matching the spatial resolution and the volume coverage. By way of example, combinations of motion detection methods and motion correction methods are feasible to the effect that imaging specifications for periods of time in which clinical sequences were used are determined from the coregistration methods, whereas, in the measurement pauses of the method having a high temporal resolution, a navigation or orientation measurement is consistently carried out which automatically generates corresponding imaging specifications in the short intervals. If the temporal resolution of the motion detection is not high enough, it is possible to interpolate between two instances of motion detection.

Furthermore, as mentioned, at least one, more if appropriate, motion information item or items for motion correction can be determined as a function of the data from at least one sensor element such as a motion detector, in particular depending on data from at least one optical and/or mechanical and/or piezoelectrical sensor element or motion detector.

The one motion information item, or the plurality of further information items, is thus not only obtained or not obtained from the data from an imaging method with a high temporal resolution, for example, but additionally or only obtained from data from an external or a plurality of external motion detectors or sensors. In this case, optical, mechanical, and piezoelectrical, or further methods can be used. By way of example, these methods can be coupled to an image recording method having a high temporal resolution, or applied on their own (simultaneously if appropriate) to the two image recording methods of the hybrid modality. The motion correction for a method with a high temporal resolution or, in particular, for the nuclear medicine method can thus be effected by additional motion information, or depend on additional data from external sensor elements such as motion detectors.

Moreover, according to at least one embodiment of the invention, the motion correction can be carried out within the scope of subsequent reconstruction of saved raw data as measured data in addition to the motion correction in real-time. Thus, in this case, that is to say at least for a portion of the data or within the scope of more precise subsequent evaluation of the data, motion correction additionally takes place not only entrained to the acquisition, but motion correction is furthermore also undertaken, within the scope of post-processing, for the already entrained, corrected data and that data that was not entrained in real time, respectively. For this purpose, the nuclear medicine raw data, and the further data if applicable, which are to be subject to motion correction are written to a memory of the computing device and/or saved externally in order to be available for the motion correction following the data recording.

According to at least one embodiment of the invention, the motion correction can be carried out in the image data space and/or in the raw data space.

The motion is already taken into account in the case of motion correction of the raw data, for example, in the case of so-called "histogramming", that is to say when binning the so-called lines of response in sinograms of PET. This results in the earliest correction possible, so that only small errors or (disadvantageous) effects are created by possible approximations and imprecision in the further processing steps.

When motion-correcting the nuclear medicine data in the form of image data, the raw data is separated into suitable periods of time, with data reconstruction being carried out without taking the motion in the individual periods of time into account. The imaging specification determined from the data from the fast image recording method is applied to the nuclear medicine data with the low spatial resolution in the image space, as a result of which a total image is generated from all time intervals. Operating with image data provides the advantage that a smaller memory volume is required and, on the other hand, a faster performance is achieved compared to approaches based on raw data due to the lower data volume. On the other hand, when using short periods of time for correcting in the image space, the reconstruction of nuclear medicine data can be error-prone due to the small amounts of statistical data available. If applicable, both methods can be combined so that one portion of the data is corrected in the raw data space and one portion is corrected in the image space, or the methods can be used in parallel for mutual verification or to complement each other.

Moreover, according to at least one embodiment of the invention, at least one attenuation correction information item available to the computational device and used for reconstructing the nuclear medicine measured data can be adapted depending on the at least one determined motion information item. This allows the attenuation correction coefficients for the reconstruction which are related to the different absorption properties of the matter in the image recording area to be tracked. The image quality of the nuclear medicine images and the quantifiability depend on the accuracy of the attenuation correction coefficients. By way of example, a corresponding attenuation correction map for recording nuclear medicine and magnetic resonance images is generated from the magnetic resonance imaging measured data. Initially, the attenuation correction data can be determined once for an examination region and can be corrected later according to the imaging specifications for the patient motion. In this case, the way in which the motion of the patient relates to static components in the region of the measured data record can be taken into account. By way of example, the static position of a patient couch or the like can be combined in a suitable manner with the moved part of the patient in an attenuation correction map.

Moreover, the invention relates to an, in particular imaging, medical device designed for simultaneously recording motion-related measured data from a patient by taking movements into account, in particular measured data with a high temporal resolution and/or measured data that can be interpolated with regard to movements, using an imaging method and/or by way of at least one sensor element, and for recording nuclear medicine measured data, in particular with a relatively low temporal resolution, and provided with a computational device for determining at least one motion information item relating to at least one movement of the patient and/or motion information relating to the inside of the body of the patient during the ongoing measured data recording by evaluating at least a portion of the previously recorded motion-related measured data, and for carrying out motion correction of at least a portion of the nuclear medicine measured data in real-time and in parallel with the measured data recording, with it in particular being a medical device which is suitable for carrying out a method of at least one embodiment as described above.

For example, the medical device is thus a hybrid modality, designed by way of example for recording magnetic resonance imaging data and nuclear medicine PET data. The data recording or image recording operation and the evaluation, respectively, are carried out by a computational device of the (imaging) medical device. The parallel recording of motion-related measured data, with a high temporal resolution or for interpolation, for example, and of nuclear medicine measured data, often having a lower temporal resolution, makes it possible to carry out motion correction for the nuclear medicine measured data, for which purpose the computational device determines at least one or more motion information items, from at least a portion of the previously recorded motion-related measured data, which are used for motion correction in real-time and is entrained to the continuing measured data recording. The measured data acquisition is thus carried out simultaneously and, in an advantageous manner, isocentrically for the two or all recording methods.

BRIEF DESCRIPTION OF THE DRAWINGS

Further advantages, features and details emerge from the example embodiments and the following drawings, in which FIG. 1 shows an outline sketch for carrying out a method according to an embodiment of the invention, FIG. 2 shows a medical imaging device according to an embodiment of the invention, FIG. 3 shows an outline sketch for carrying out prospective motion correction in the case of a method according an embodiment of to the invention, FIG. 4 shows an outline sketch of entrained correction of a standardized image in the case of a method according to an embodiment of the invention.

DETAILED DESCRIPTION OF THE EXAMPLE EMBODIMENTS

Figure 5:
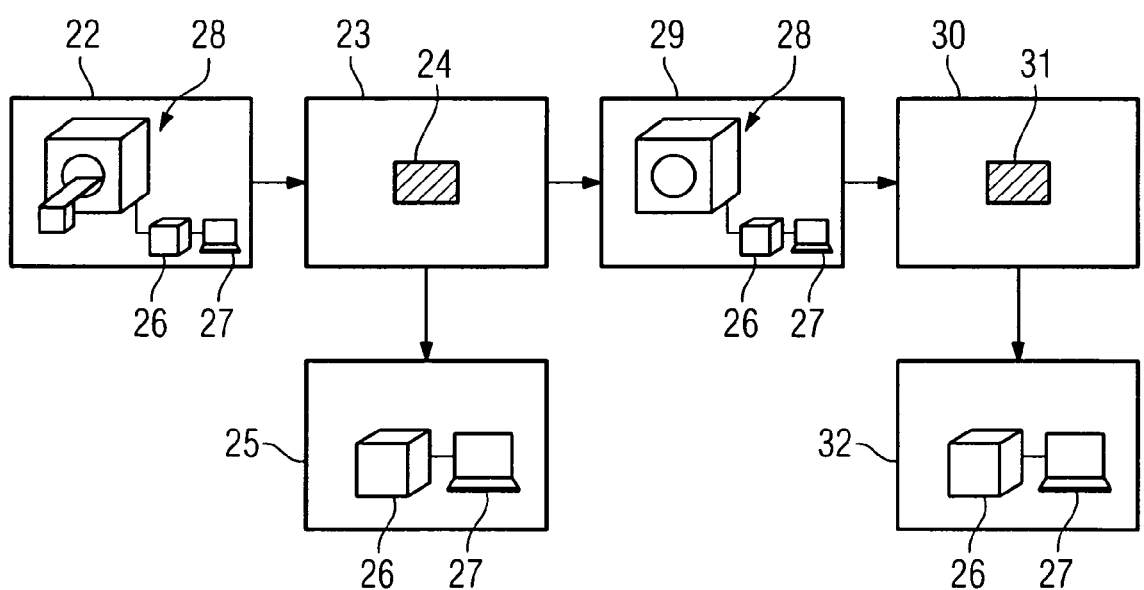
FIG. 5 shows an outline sketch for k-space-based motion correction according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an outline sketch for carrying out a method according to an embodiment of the invention.

In this case, box a represents the recording of nuclear medicine measured data by means of a medical device, while box b represents the simultaneous recording of motion-related measured data with a high temporal resolution and measured data which can be interpolated with regard to movements by way of the medical device.

The data accordingly recorded in parallel is used to determine at least one movement of the patient and/or motion information relating to the inside of the body of the patient, as symbolized by box c, during the ongoing measured data recording by evaluating at least a portion of the previously recorded motion-related measured data by way of a computational device of the medical device.

Thus, within the scope of the method according to an embodiment of the invention, simultaneous and isocentric measured data acquisition is first of all carried out by way of a hybrid modality, for example a modality designed for recording nuclear medicine data and magnetic resonance data having a high temporal resolution. Here, the data from the method with the high temporal resolution is used at least in part to obtain motion information related to periodic movements, such as respiration, or other motions in the body of the patient or by the patient.

According to box d, this motion information is finally used in order to carry out motion correction for at least a portion of the nuclear medicine measured data in real-time by means of the computational device in parallel with recording the measured data depending on the at least one determined motion information item. Thus, according to box d, motion correction for nuclear medicine data, that is to say data that generally has the lower temporal resolution, is carried out using the motion information determined according to box c. Entrained motion correction is thus possible in real-time. According to an embodiment of the invention, the nuclear medicine data quality is improved by detecting patient motion from the data from the method for determining the motion-related measured data and using said method for reconstructing the nuclear medicine data.

FIG. 2 shows a medical imaging device 1 according to an embodiment of the invention. The medical imaging device 1 according to an embodiment of the invention illustrated here is designed to record magnetic resonance imaging data and data from the method of positron emission tomography. In other exemplary embodiments, it is of course possible for devices to be provided which combine other (possibly non-imaging) methods having a high temporal resolution or those providing data suitable for interpolation with possibly other or a number of nuclear medicine recording methods.

The medical imaging device 1 includes a tomography scanner 2 for actually recording the measured data and a patient couch 3. A patient 4, who voluntarily or involuntarily undergoes motion during the measured data recording by the tomography scanner 2, for example moving his limbs or undergoing respiratory motions or cardiac motions, which the patient 4 himself cannot influence or can exert only little influence on, is positioned on the patient couch 3. These movements by the patient 4 or within the body of the patient 4 influence the image quality of the images from the positron emission tomography, so that accordingly correction with regard to the motions of the patient 4 is desirable.

This is carried out by using the computational device 5 which is connected to the tomography scanner 2 via a data connection and additionally has a screen 6 with an input apparatus for an operator who is not illustrated here. The computational device 5 is used to determine a motion information item or a series of motion information items relating to the movements of the patient 4 from the magnetic resonance data with a high temporal resolution during ongoing measured data recording using the tomography scanner 2. This motion information is subsequently used by the computational device 5 to subject the nuclear medicine measured data from the tomography scanner 2 to motion correction in real-time, entrained to the still ongoing measured data recording. This does not necessarily mean that all PET measured data has to be motion corrected; likewise, this does not necessarily mean that all magnetic resonance imaging measured data is used to carry out the motion correction. Generally, as in this case, the magnetic resonance imaging measured data is used at least in part to generate anatomical images and only in a further part to carry out the entrained motion correction of the method according to an embodiment of the invention.

FIG. 3 shows an outline sketch for carrying out prospective motion correction in the case of a method according to an embodiment of the invention. In this case, box 7 symbolizes the presence of motion information, this motion information being able to relate to a partial area of the image record volume or to the whole examination area. As indicated by the arrows 8, this motion information according to box 7 is applied to the nuclear medicine measured data 10 arriving according to the arrows 9, this motion correction of the nuclear medicine measured data 10 being carried out in real-time, entrained to the further measured data recording. The motion correction of the nuclear medicine measured data 10 depending on the motion information according to box 7 is carried out until a new motion information item according to box 11 is present. When this new motion information according to box 11 is present, this new motion information is used, according to the arrows 12, to correct the nuclear medicine measured data 14 then arriving, as indicated by the arrows 13. The incoming data can thus be processed directly without a waiting period, so that even if measured data recording is canceled, all recorded nuclear medicine data 10, 14 is already motion corrected.

FIG. 4 shows an outline sketch for the entrained correction of a standardized image 15 in box 16 in the case of a method according to an embodiment of the invention. The standardized image 15, which is an image used to detect motion, is itself prospectively corrected in this case. This means that a reference coordinate system 17, which is indicated here in box 18 and in which the images of the method are recorded with a high temporal resolution, is entrained to each detected motion. By way of this entrainment, a new standardized image 20 is obtained according to box 19 and provides the advantage that even in the case of high motion amplitude, the look of this standardized image 20 is very similar compared to the preceding standardized image 15, so that reliable registration of the current motion state is simplified.

The correction information for the nuclear medicine method for measured data recording according to box 21 is then combined, as is intended to be indicated by the arrows, from the rotation and translation of the reference coordinate system 17 and the rotation and translation of the respectively recorded object (patient or recording area of the patient) in this system.

FIG. 5 illustrates an outline sketch for the k-space-based motion correction according to the invention. According to box 22, parallel recording of nuclear medicine data and motion-related data, for example a method with a high temporal resolution, takes place in this case. This data recording is carried out simultaneously and isocentrically. In this case, a navigation scan 24 is recorded at particular time intervals or particular points in time, as indicated by box 23, in order to carry out motion correction according to box 25, using a computational device 26 having a screen 27 belonging to a medical imaging device 28.

A navigation scan 24 permits information to be obtained about rigid body motion in only a few milliseconds, and thus allows temporally very high-resolution motion correction according to box 25 to be carried out. The record of the navigation scan 24 is incorporated into the normal clinical image recording operation by way of the medical imaging device 28, which operation is continued in parallel, as shown by box 29. According to box 30, a navigation scan 31 is recorded again after a determined lapse of time and is used for the renewed motion correction according to box 32. It is thus possible to detect and correct movements in parallel with the nuclear medicine data recording and the performance of standard clinical recording operations using the method with high temporal resolution.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for recording measured data from a patient by taking movements into account by use of a medical device designed both for recording motion-related measured data and for recording nuclear medicine measured data, the method comprising:

recording nuclear medicine measured data using the medical device;

simultaneously recording motion-related measured data using the medical device, the motion related data being at least one of magnetic resonance imaging data, computed tomography data and ultrasound data;

determining at least one motion information item relating to at least one of at least one movement of the patient and at least one movement inside the body of the patient during the measured data recording by evaluating at least a portion of previously recorded motion-related measured data using a computational device of the medical device; and carrying out motion correction for at least a portion of the nuclear medicine measured data in real-time using the computational device in parallel with recording the measured data depending on the at least one determined motion information item.

2. The method as claimed in claim 1, wherein at least one of the motion correction is carried out prospectively and a determined motion information item for carrying out motion correction for newly recorded measured data is adapted.

3. The method as claimed in claim 1, wherein the motion correction is additionally carried out for at least a portion of the motion-related measured data.

4. The method as claimed in claim 3, wherein the motion correction is carried out such that a reference coordinate system is entrained to the motion-correction for recording the motion-related measured data.

5. The method as claimed in claim 4, wherein the motion correction for at least a portion of the nuclear medicine measured data is carried out taking into account at least one of the translation and rotation of the reference coordinate system, and the at least one of the translation and rotation of at least one recording object in the reference coordinate system.

6. The method as claimed in claim 1, wherein at least one of at least one of magnetic resonance imaging data, computed tomography data, ultrasound data, and sensor data, is recorded as motion-related measured data, and at least one of positron emission tomography data and single photon emission computed tomography data is recorded as nuclear medicine measured data.

7. The method as claimed in claim 6, wherein, in the case of recording magnetic resonance data as motion-related measured data, at least one motion information item is determined in reciprocal magnetic resonance imaging (MRI) k-space.

8. The method as claimed in claims 7, wherein the motion information in MRI k-space is determined on the basis of at least one recorded navigation scan.

9. The method as claimed in claim 1, wherein the motion-related measured data and the nuclear medicine measured data are recorded at least one of isocentrically and with synchronized timestamps.

10. The method as claimed in claim 1, wherein at least one imaging specification for the motion correction is determined from the at least one motion information item.

11. The method as claimed in claim 1, wherein at least one motion information item is determined at least one of using at least one motion detection module provided for recording the motion-related measured data, using at least one measured data record carried out using a reduced spatial resolution, and within the scope of keyhole measured data recording.

12. The method as claimed in claim 1, wherein at least one of rigid and elastic motion correction is carried out.

13. The method as claimed in claim 1, wherein, within the scope of the simultaneous recording of the motion-related measured data, at least one of at least one standard measurement protocol, at least one attenuation correction measurement and at least one navigation scan is recorded at least one of at points in time and at fixed time intervals.

14. The method as claimed in claim 1, wherein the motion correction is carried out within the scope of a subsequent reconstruction of saved raw data as measured data in addition to motion-correction in real-time.

15. The method as claimed in claim 1, wherein the motion correction is carried out in at least one of the image data space and the raw data space.

16. The method as claimed in claim 1, wherein at least one attenuation correction information item serving to reconstruct the nuclear medicine measured data and which is available to the computational device is adapted depending on the at least one determined motion information item.

17. A medical device, designed for simultaneously recording motion-related measured data from a patient by taking movements into account, using at least one of an imaging method and by way of at least one sensor element, and for recording nuclear medicine measured data, the medical device, comprising:
a computational device to determine at least one of at least one motion information item relating to at least one movement of the patient and motion information relating to the inside of the body of the patient during the ongoing measured data recording by evaluating at least a portion of the previously recorded motion-related measured data, and to carry out motion correction of at least a portion of the nuclear medicine measured data in real-time and in parallel with the measured data recording, wherein the motion related measured data is at least one of magnetic resonance imaging data, computed tomography data and ultrasound data.

18. The method as claimed in claim 2, wherein the motion correction is carried out such that motion correction for newly recorded measured data is carried out depending on a determined motion information item until a corresponding new motion information item is present.

19. The method as claimed in claim 2, wherein the motion correction is additionally carried out for at least a portion of the motion-related measured data.

20. The method as claimed in claim 10, wherein at least one imaging specification for the motion correction is determined from the at least one motion information item within the scope of automatic motion detection for recording the motion-related measured data record.

* * * * *